US010716678B2

(12) United States Patent
Stampfli et al.

(10) Patent No.: US 10,716,678 B2
(45) Date of Patent: Jul. 21, 2020

(54) INTERVERTEBRAL IMPLANT

(71) Applicant: DePuy Synthes Products, Inc., Raynham, MA (US)

(72) Inventors: Christian Stampfli, Zuchwil (CH); Mario Wyss, Egerkingen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 254 days.

(21) Appl. No.: 15/709,768

(22) Filed: Sep. 20, 2017

(65) Prior Publication Data

US 2018/0078380 A1     Mar. 22, 2018

Related U.S. Application Data

(60) Provisional application No. 62/397,217, filed on Sep. 20, 2016.

(51) Int. Cl.
*A61F 2/44*        (2006.01)
*A61F 2/46*        (2006.01)
*A61F 2/30*        (2006.01)

(52) U.S. Cl.
CPC ............. *A61F 2/442* (2013.01); *A61F 2/447* (2013.01); *A61F 2/4455* (2013.01); *A61F 2/4601* (2013.01); *A61F 2/4611* (2013.01); *A61F 2/30771* (2013.01); *A61F 2002/30266* (2013.01); *A61F 2002/30593* (2013.01); *A61F 2002/30616* (2013.01); *A61F 2002/30777* (2013.01); *A61F 2002/30784* (2013.01); *A61F 2002/30836* (2013.01); *A61F 2002/449* (2013.01)

(58) Field of Classification Search
CPC .... A61F 2/44; A61F 2/442; A61F 2/46; A61F 2/4601; A61F 2/4611
See application file for complete search history.

(56) References Cited

U.S. PATENT DOCUMENTS

| | | | | |
|---|---|---|---|---|
| 5,888,227 | A * | 3/1999 | Cottle | A61F 2/442 623/17.16 |
| 7,998,212 | B2 * | 8/2011 | Schwab | A61F 2/4465 623/17.11 |
| 8,287,597 | B1 * | 10/2012 | Pimenta | A61B 17/320016 623/17.16 |
| 8,308,734 | B2 | 11/2012 | Evans et al. | |
| 2003/0014110 | A1 | 1/2003 | Ralph et al. | |
| 2006/0015184 | A1 | 1/2006 | Winterbottom et al. | |
| 2012/0277866 | A1 * | 11/2012 | Kalluri | A61F 2/442 623/17.16 |

(Continued)

FOREIGN PATENT DOCUMENTS

WO     2010/107692 A1     9/2010
WO     2016/026057     2/2016

*Primary Examiner* — Christopher J Beccia
(74) *Attorney, Agent, or Firm* — BakerHostetler

(57) ABSTRACT

An intervertebral implant is disclosed. The implant can be made of Titanium or alloys thereof. A kit of intervertebral implants can be included having different lordotic profiles or having no lordotic profile. The intervertebral implants of the kit have endplates with thicknesses suitable to prevent the titanium endplates from being too stiff. The intervertebral implants can have apertures that extend through the endplates, but sufficient surface area at the outer surfaces of the endplates to avoid subsidence into the respective vertebral body.

20 Claims, 5 Drawing Sheets

(56) References Cited

U.S. PATENT DOCUMENTS

2014/0330383 A1\* 11/2014 Wimberley ........... A61F 2/4611
                                                                 623/17.16
2015/0182346 A1    7/2015 Emerick et al.

\* cited by examiner

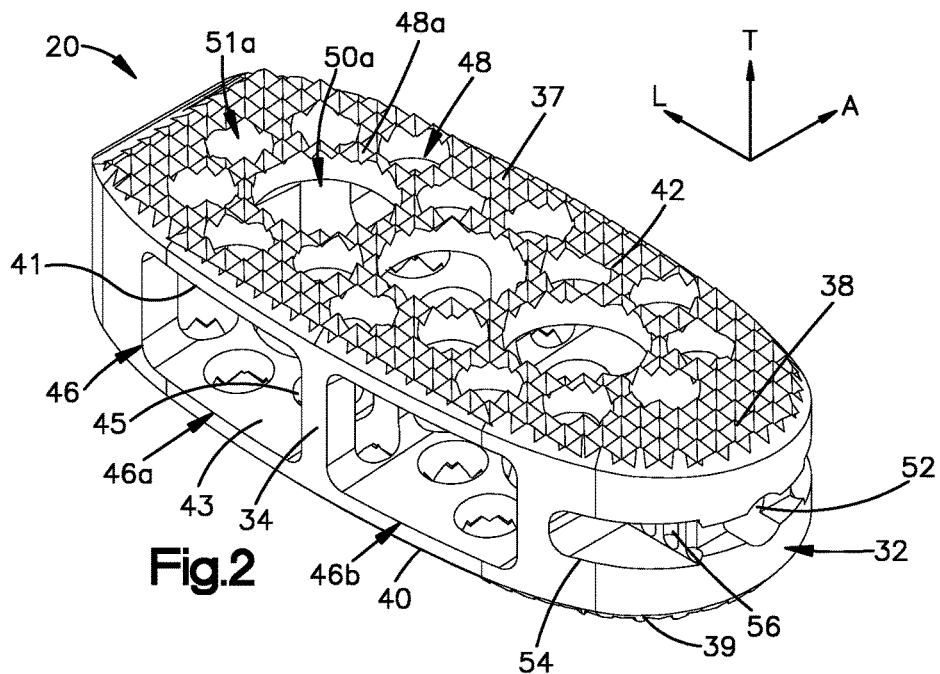
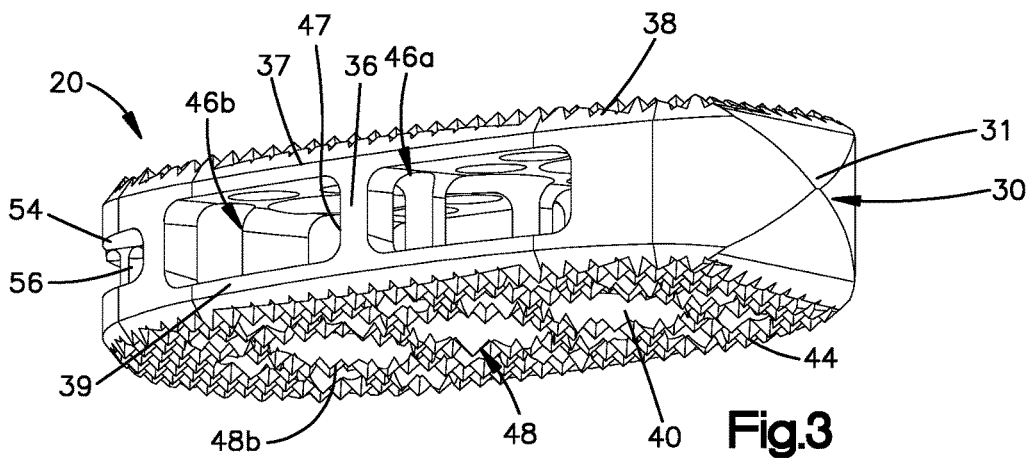
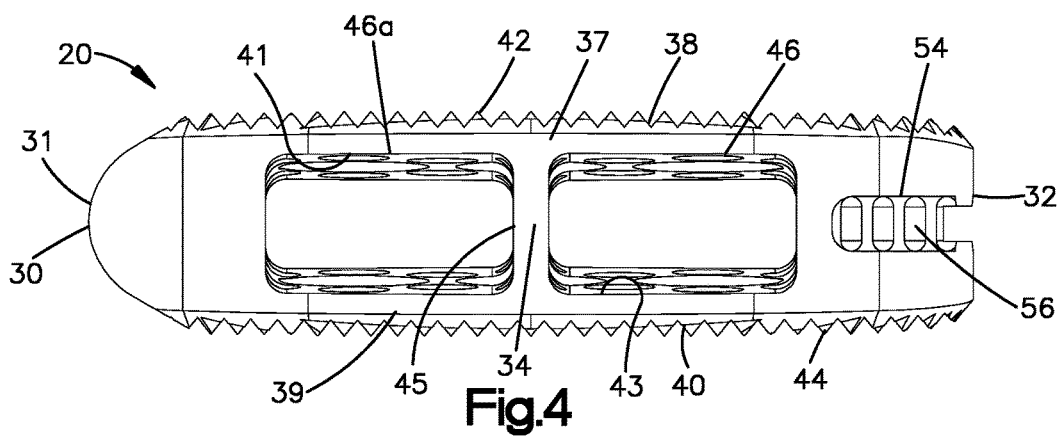

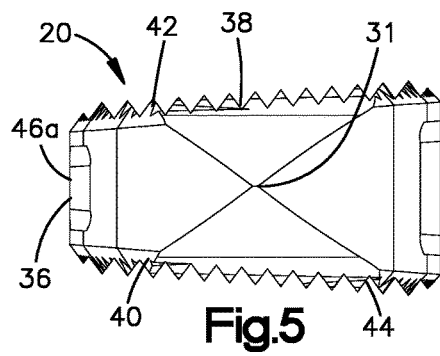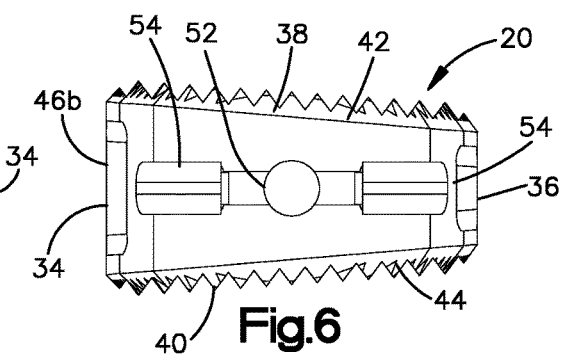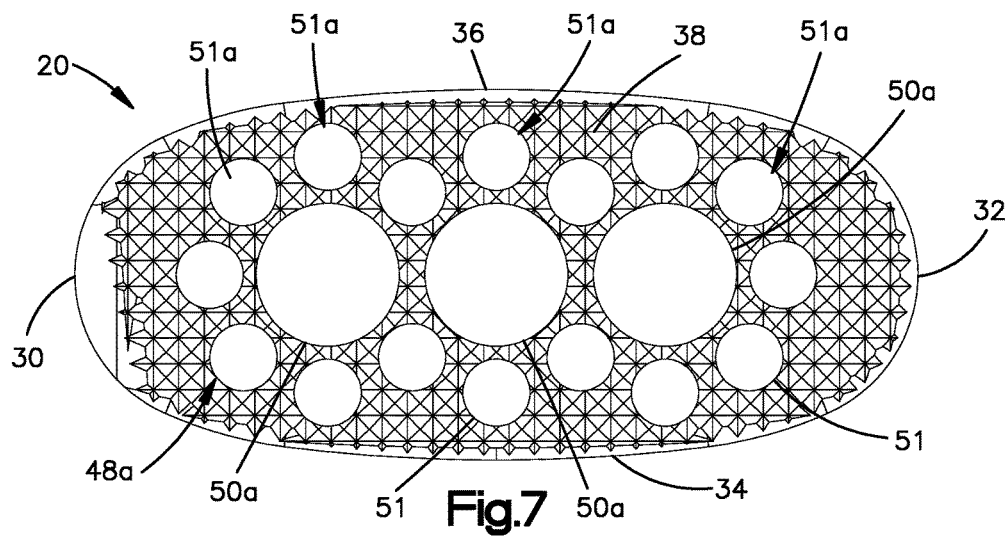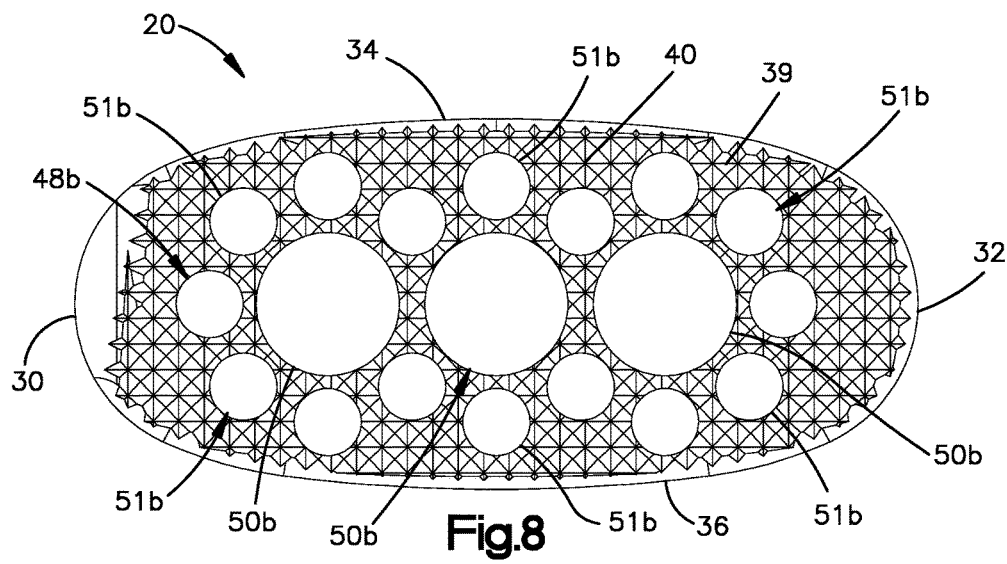

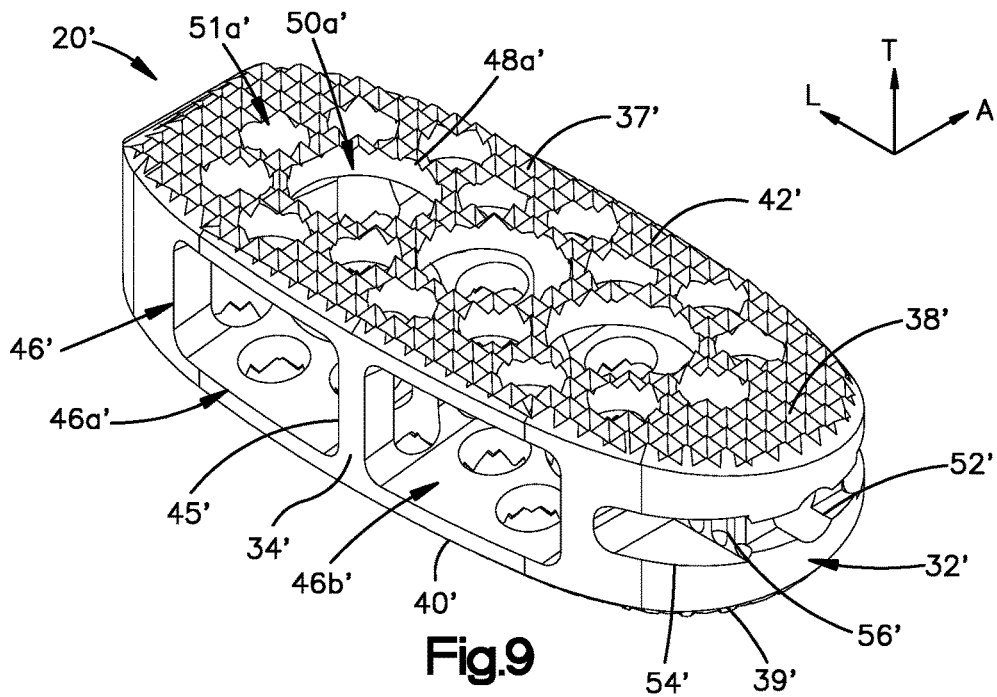
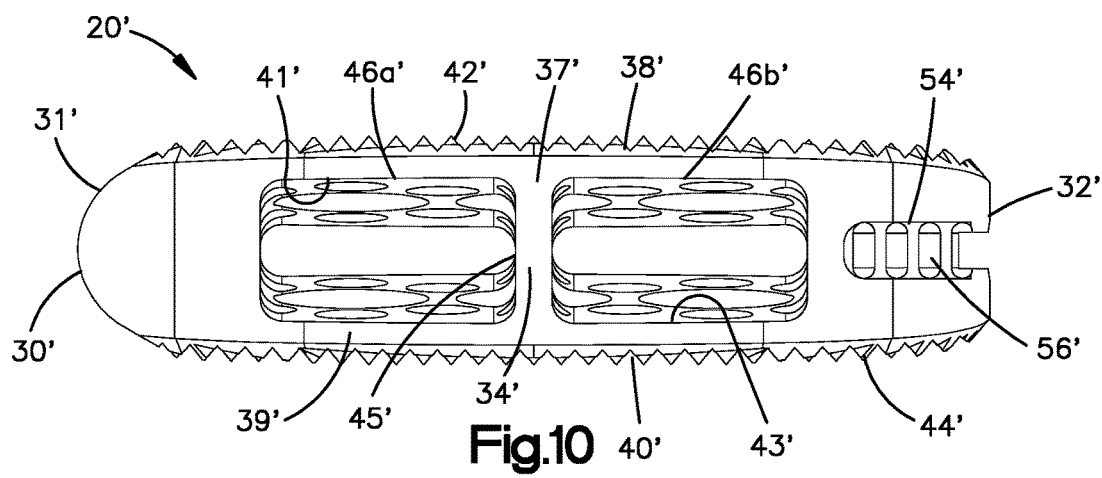
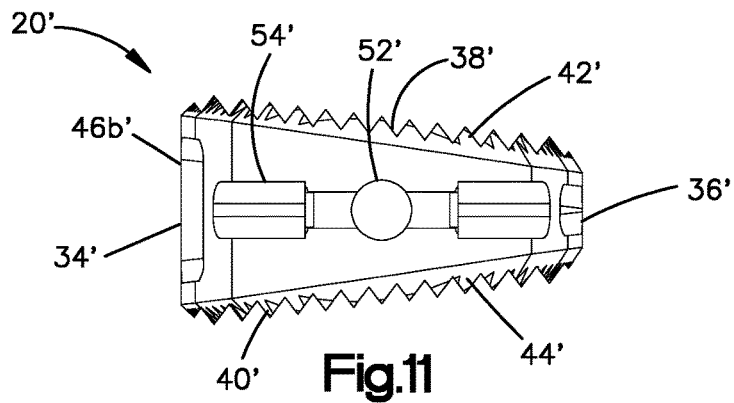

INTERVERTEBRAL IMPLANT

CROSS-REFERENCE TO RELATED APPLICATIONS

This claims priority to U.S. Patent Application Ser. No. 62/397,217 filed Sep. 20, 2016, the disclosure of which is hereby incorporated by reference as if set forth in its entirety herein.

BACKGROUND

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus with its cushioning qualities. These nucleus pulposus cells may also secrete small amounts of cytokines as well as matrix metalloproteinases (MMPs). These cytokines and MMPs help regulate the metabolism of the nucleus pulposus cells.

In some instances of degenerative disc disease (DDD), gradual degeneration of the intervertebral disc is caused by mechanical instabilities in other portions of the spine. In these instances, increased loads and pressures on the nucleus pulposus cause the cells within the disc (or invading macrophages) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of proinflammatory cytokines and/or MMPs that may cause nerve irritation and pain.

As DDD progresses, toxic levels of the cytokines and MMPs present in the nucleus pulposus begin to degrade the extracellular matrix. In particular, the MMPs (as mediated by the cytokines) begin cleaving the water-retaining portions of the proteoglycans, thereby reducing their water-retaining capabilities. This degradation leads to a less flexible 2 nucleus pulposus, and so changes the loading pattern within the disc, thereby possibly causing delamination of the annulus fibrosus. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with an intervertebral implant that restores disc height and allows for bone growth therethrough for the fusion of the adjacent vertebrae. These devices are commonly called "fusion devices".

SUMMARY

In accordance with one aspect of the present disclosure, a kit of intervertebral implants can each be configured to be inserted into an intervertebral space. Each intervertebral implant of the kit can include a leading end and a trailing end, arranged such that the leading end is spaced from the trailing end in an insertion direction into the intervertebral space. Each intervertebral implant of the kit can further include an anterior side wall and a posterior side wall each extending between the leading end and the trailing end, wherein the anterior and posterior side walls are opposite each other along a lateral direction that is perpendicular to the insertion direction. Each intervertebral implant of the kit can further include upper and lower endplates each made of Titanium or an alloy thereof and spaced from each other along a transverse direction that is perpendicular to each of the insertion direction and the lateral direction. Each of the endplates can define a respective outer surface that is configured to abut respective superior and inferior vertebral bodies when the implant is disposed in the intervertebral space. The anterior side wall of a first intervertebral implant of the kit can have a height greater than that of the posterior side wall along the transverse direction, such that the upper and lower endplates of the first intervertebral implant define a first angle with respect to each other as they extend along the lateral direction, and each of the upper and lower endplates of the first intervertebral implant define respective thicknesses at the anterior side wall. The anterior side wall of a second intervertebral implant of the kit can have a height greater than that of the posterior side wall along the transverse direction, such that the upper and lower endplates of the second intervertebral implant define a second angle with respect to each other as they extend along the lateral direction that is greater than the first angle. Each of the upper and lower endplates of the second intervertebral implant can define respective thicknesses at the anterior side wall that are equal to the respective thicknesses of the upper and lower endplates of the first intervertebral implant at the anterior side wall.

BRIEF DESCRIPTION OF THE DRAWINGS

The foregoing summary, as well as the following detailed description of embodiments of the application, will be better understood when read in conjunction with the appended drawings. For the purposes of illustrating the methods, implants and systems of the present application, there is shown in the drawings preferred embodiments. It should be understood, however, that the application is not limited to the precise methods, implants, and systems shown. In the drawings:

FIG. 2 is a top perspective view of the intervertebral implant illustrated in FIG. 1;

FIG. 3 is a bottom perspective view of the intervertebral implant illustrated in FIG. 1;

FIG. 4 is a side elevation view of the intervertebral implant illustrated in FIG. 1;

FIG. 5 is a front elevation view of the intervertebral implant illustrated in FIG. 1;

FIG. 6 is a rear elevation view of the intervertebral implant illustrated in FIG. 1;

FIG. 7 is a top plan view of the intervertebral implant illustrated in FIG. 1;

FIG. 8 is a bottom plan view of the intervertebral implant illustrated in FIG. 1;

FIG. 9 is a perspective view of an intervertebral implant similar to the intervertebral implant illustrated in FIG. 1, but sloped in accordance with an alternative embodiment;

FIG. 10 is a side elevation view of the intervertebral implant illustrated in FIG. 9;

FIG. 11 is a rear end elevation view of the intervertebral implant illustrated in FIG. 9;

DETAILED DESCRIPTION

Figure 1:
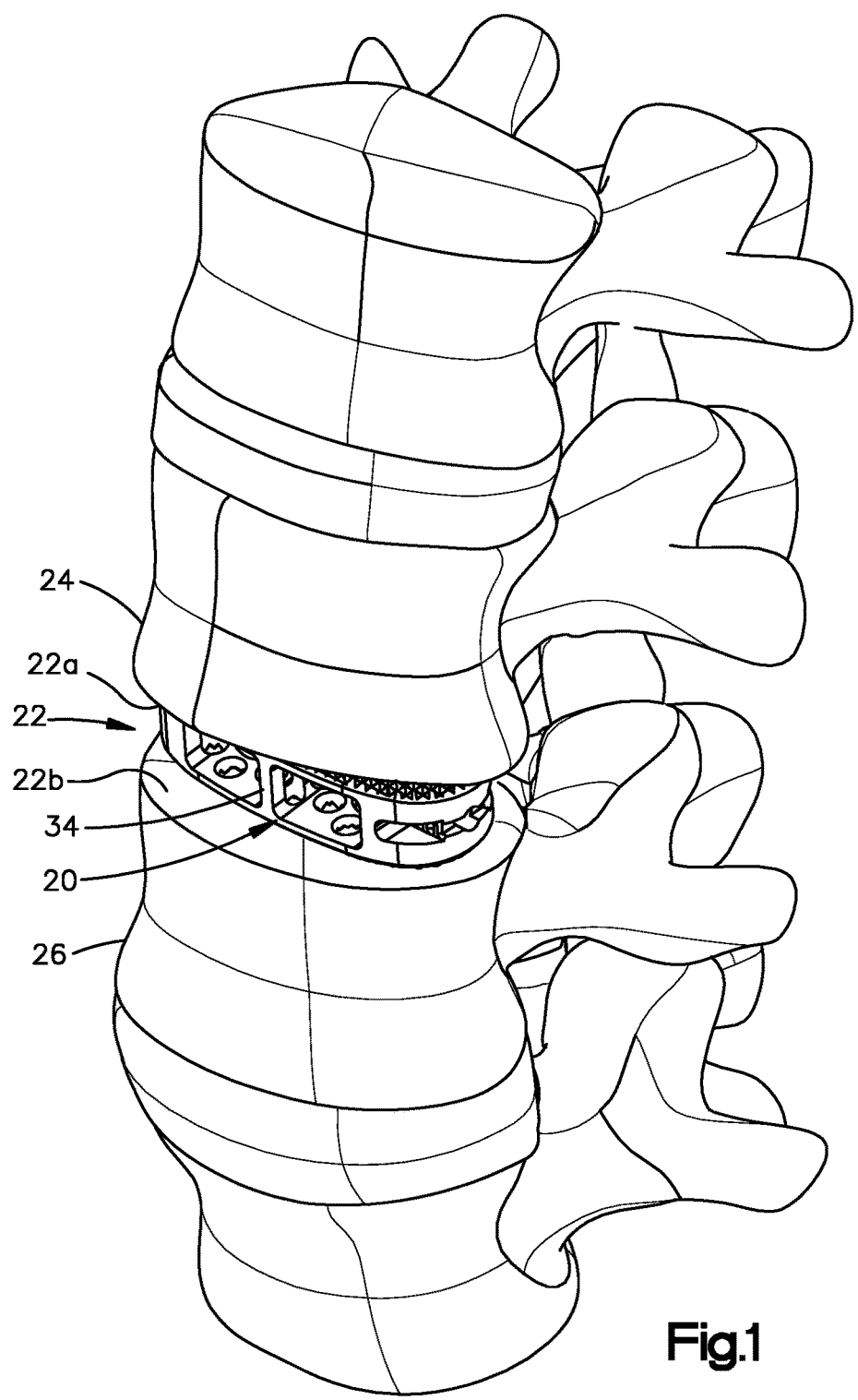
FIG. 1 is a perspective view of an intervertebral implant implanted into an intervertebral space.

Referring to FIG. 1, an intervertebral implant 20 is implanted in an intervertebral disc space 22 that is defined by a first vertebral body 24 and a second vertebral body 26. The first vertebral body 24 can be referred to as a superior vertebral body, and the second vertebral body 26 can be referred to as an inferior vertebral body. The disc space 22 has been prepared such that at least a portion up to all of the natural intervertebral disc has been removed, thereby creating a void that is configured to receive the intervertebral implant 20. The first vertebral body 24 can define a superior vertebral endplate surface 22a of the intervertebral space 22. The second vertebral body 26 can define an inferior vertebral endplate surface 22b of the intervertebral space 22.

Referring now also to FIGS. 2-8, and as described in more detail below, the present disclosure recognizes that it may be desirable to construct a Titanium intervertebral implant. A Titanium intervertebral implant can be made from Titanium or one or more alloys thereof. The Titanium can be a commercially pure Titanium. For instance, the present disclosure recognizes that Titanium implants allow for bone to grow into the implant as opposed to intervertebral implants made from poly-ether-ether-ketone (PEEK). However, as will become appreciated from the description below, because Titanium is a harder material than PEEK, the intervertebral implants 20 described herein have structural features that are different than conventional PEEK implants, including the PEEK intervertebral implant of the Oracle® Cage system that is commercially available from DePuy Synthes, Inc., a company of Johnson and Johnson having a place of business in New Brunswick, N.J. Thus, while the implant 20 has certain features that render the implant 20 especially suitable for Titanium construction, it should be appreciated that the implant 20 can be made from any suitable alternative biocompatible material as desired. In one example, the implant 20 can be made from the material of the intervertebral implant of the SynCage™ system that is commercially available from DePuy Synthes, a company of Johnson and Johnson having a place of business in New Brunswick, N.J. Further, the implant 20 can be made from the material of the intervertebral implant of the Oracle® Cage system.

The intervertebral implant 20 defines a leading end 30, and a trailing end 32 opposite the leading end 30 along a central axis of the implant 20. The implant 20 can be elongate along the central axis. The intervertebral implant 20 can be inserted into the intervertebral disc space 22 in an insertion direction that is defined from the trailing end 32 to the leading end 30. Thus, the leading end 30 can be said to be spaced from the trailing end 32 in a direction of insertion into the intervertebral disc space 22. The leading end 30 can define a tapered bullet-shaped nose 31. The insertion direction can be oriented along a longitudinal direction L that includes both the insertion direction and a rearward direction that is opposite the insertion direction. In one example, the nose 31 can be inwardly tapered both along one or both of a transverse direction T and a lateral direction L as it extends in the insertion direction. For instance, the nose 31 can be rounded. In one example, the nose 31 can be configured as in the Oracle® Cage system that is commercially available from DePuy Synthes, Inc., a company of Johnson and Johnson having a place of business in New Brunswick, N.J. It should be appreciated, of course, that the leading end 30 can define any suitable alternative shape as desired. The transverse direction T is oriented substantially perpendicular with respect to the longitudinal direction L. The lateral direction A is oriented substantially perpendicular with respect to each of the transverse direction T and the longitudinal direction L.

In one example, the intervertebral implant 20 can be inserted into the intervertebral disc space 22 along a lateral approach into the intervertebral disc space. Thus, the insertion direction into the intervertebral disc space 22 can be defined by the anatomical lateral direction. The lateral approach can be a transpsoas approach into the lumbar region of the spine. Thus, the first and second vertebral bodies 24 and 26 can be defined by lumbar vertebrae. It should be appreciated, however, that the intervertebral implant 20 is not to be limited to a lumber implant, unless otherwise indicated. For instance, certain principles of the present disclosure can be applicable to an implant configured for insertion into a thoracic intervertebral disc space. Alternatively or additionally, certain principles of the present disclosure can be applicable to an implant configured for insertion into a cervical intervertebral disc space. It should be further appreciated that the implant 20 can be inserted into the intervertebral disc space along any approach as desired.

The leading end 30 and the trailing end 32 can be spaced from each other along the longitudinal direction L. Thus, the intervertebral implant 20 can be elongate along the longitudinal direction L. The intervertebral implant 20 further defines a first side wall 34 and a second side wall 36 that each extends from the leading end 30 to the trailing end 32. The intervertebral implant 20 can define a footprint that is defined by the leading end 30, the trailing end 32, the first side wall 34, and the second side wall 36. The footprint can be sized and shaped so as to fit in the intervertebral disc space 22.

The implant 20 can be configured to be implanted into the intervertebral space 22 such that the first side wall 34 is disposed anterior of the second side wall 36, and the second side wall 36 is thus disposed posterior of the first side wall 34. Thus, the first side wall 34 can be referred to as an anterior side wall. The second side wall 36 can be referred to as a posterior side wall. With respect to a view of the trailing end 32 of the implant 20 in the insertion direction, the first side wall 34 is on the left side of the implant 20, and the second side wall 36 is on the right side of the implant 20. The first and second side walls 34 and 36 can be opposite each other along the lateral direction A. The first and second side walls 34 and 36 can define respective inner side surfaces that generally face each other along the lateral direction A, and respective outer side surfaces opposite the respective inner side surfaces. Thus, the outer side surfaces face away from each other along the lateral direction A.

The intervertebral implant 20 further includes an upper endplate 37 and a lower endplate 39 opposite the upper endplate 37 along the transverse direction T. The upper endplate 37 defines an upper outer surface 38 that is configured to face the superior vertebral endplate surface 22a when the implant 20 is disposed in the intervertebral space 22. For instance, the upper outer surface 38 can be configured to abut the superior vertebral endplate surface 22a. In one example, the upper outer surface 38 can be configured to grip the superior vertebral endplate surface 22a. For instance, the upper outer surface 38 can define upwardly extending teeth 42 that are configured to grip the superior vertebral surface 22a. The upper endplate 37 can further define an upper inner surface 41 that is opposite the upper outer surface 38 along the transverse direction T.

Similarly, the lower endplate 39 defines a lower outer surface 40 that is configured to face the inferior vertebral endplate surface 22b when the implant 20 is disposed in the intervertebral space 22. For instance, the lower outer surface 40 can be configured to abut the inferior vertebral endplate surface 22b. In one example, the lower outer surface 40 can be configured to grip the inferior vertebral endplate surface 22b. For instance, the lower outer surface 40 can define downwardly extending teeth 44 that are configured to grip the inferior vertebral surface 22b. The lower endplate 39 can further define a lower inner surface 43 that is opposite the lower outer surface 40 along the transverse direction T Thus, the lower inner surface 43 can generally face the upper inner surface 41 along the transverse direction T. In this regard, the lower inner surface 43 and the upper inner surface 41 can face the transverse direction T or a direction oblique to the transverse direction T. The teeth 42 and 44 can be configured to engage the first and second vertebral bodies 24 and 26, respectively, so as to prevent or minimize migration of the implant 20 in the intervertebral space 22 after implantation. The teeth 42 and 44 can be configured as in the intervertebral implant of the SynCage™ system.

The upper and lower endplates 37 and 39 can be spaced from each other along the transverse direction T so as to define a hollow interior therebetween. The intervertebral implant 20 can define at least one side aperture 46 that extends through one or both of the first and second side walls 34 and 36 at least toward the other of the first and second side walls 34 and 36 along the lateral direction A. Thus, the at least one side aperture 46 can be referred to as a lateral bone graft aperture. The side aperture 46 extending through the first side wall 34 can be referred to as an anterior side aperture. The side aperture 46 extending through the second side wall 36 can be referred to as an anterior side aperture.

The at least one side aperture 46 can extend from the respective outer side surface to the respective inner side surface. Accordingly, the at least one side aperture 46 can be open go the hollow interior. The at least one side aperture 46 can be a bone graft aperture that is configured to receive bone graft material to assist in fusion of the intervertebral implant 20 with either or both of the first and second vertebral bodies 24 and 26. The bone graft material can fuse to the superior and inferior vertebral surfaces 22a and 22b of the intervertebral disc space 22. In this regard, the implant 20 can be referred to as a fusion cage that is configured to fuse to the first and second vertebral bodies 24 and 26. Further, the titanium endplates 37 and 39 can allow bone to grow therein to fuse the intervertebral implant 20 to the first and second vertebral bodies 24 and 26.

The at least one side aperture 46 can extend between the first and second endplates 37 and 39. In one example, the at least one side aperture 46 can extend through the implant 20 from the first side wall 34 to the second side wall 36 along the lateral direction A. Thus, the at least one side aperture 46 can be referred to as a through hole. In particular, the at least one side aperture can be referred to as a lateral through hole.

Alternatively, the at least one side aperture 46 can extend from the first side wall 34 along the lateral direction A, and can terminate without passing through the second side wall 36. Otherwise stated, the at least one side aperture 46 can define a first opening for the insertion of bone graft material at one side of the implant 20, but does not define a second opening opposite the first opening with respect to the lateral direction A. Thus, in one example the at least one side aperture 46 can extend through the first side wall 34, but not through the second side wall 36. As bone graft material is inserted through the at least one side aperture 46, the bone graft material is forced through vertical bone graft holes that extend through one or both of the upper and lower endplates 37 and 39, respectively, as described in more detail below.

The at least one side aperture 46 can include first and second side apertures 46a and 46b spaced from each other along the longitudinal direction L. The first side wall 34 can define a first rib 45 that separates the first and second side apertures 46a and 46b from each other along the longitudinal direction L. The rib 45 can extend from the upper endplate 37 to the lower endplate 39. The rib 45 can be oriented along the transverse direction T. Similarly, when the second side wall 36 defines respective first and second side apertures 46a and 46b, the second side wall 36 can define a second rib 47 that separates the first and second apertures 46a and 46b from each other. The second rib 47 can extend from the upper endplate 37 to the lower endplate 39. The second rib 47 can be oriented along the transverse direction T. The ribs 45 and 47 can define a thickness along a direction that is perpendicular to the transverse direction T. The thickness can increase as the lordotic angle of the intervertebral implant 20 increases, as described in more detail below. Thus, a first intervertebral implant 20 of a kit can have a first lordotic angle, and the second intervertebral implant 20 of the kit can have a second lordotic angle greater than the first lordotic angle. The thickness of one or both of the ribs 45 and 47 of the second intervertebral implant 20 of the kit can be greater than the respective thickness of one or both of the ribs 45 and 47 of the first intervertebral implant 20 of the kit. The thickness can be measured along the longitudinal direction L. Alternatively or additionally, the first intervertebral implant 20 of a kit can define a first length along the longitudinal direction L, and the second intervertebral implant 20 of the kit define have a second length along the longitudinal direction L that is greater than the first length. For instance, the first and second lengths can be between and including approximately 40 mm and approximately 60 mm.

Alternatively or additionally still, the first intervertebral implant 20 of a kit can define a first width along the lateral direction A, and the second intervertebral implant 20 of the kit can define a second width along the lateral direction A that is greater than the first width. In one example, the first and second widths can be between and including approximately 22 mm and approximately 26 mm. The thickness of one or both of the ribs 45 and 47 of the second intervertebral implant 20 of the kit can be greater than the respective thickness of one or both of the ribs 45 and 47 of the first intervertebral implant 20 of the kit. The thickness can be measured along the longitudinal direction A.

The first side aperture 46a can be spaced from the second side aperture 46b in the insertion direction. Thus, the first side aperture 46a can be disposed between the second side aperture 46b and the leading end 30 with respect to the longitudinal direction L. Similarly, the second side aperture 46b can be disposed between the first side aperture 46a and the trailing end 32 with respect to the longitudinal direction L. While first and second side apertures 46a and 46b are shown in accordance with one example, it should be appreciated that the at least one side aperture 46 can include any number of apertures as desired.

The intervertebral implant 20 can further include at least one aperture 48 that extends through one or both of the upper and lower endplate 37 and 39 along the transverse direction T. For instance, the at least one aperture 48 can extend through the upper endplate 37 from the upper outer surface 38 to the upper inner surface 41. Alternatively or additionally, the at least one aperture 48 can extend through the lower endplate 39 from the lower outer surface 40 lower inner surface 43. Thus, the at least one aperture 48 can be referred to as a transverse or vertical aperture. The at least one vertical aperture 48 can be a bone graft aperture that is configured to receive bone graft material to assist in fusion of the intervertebral implant 20 with either or both of the first and second vertebral bodies 24 and 26. In particular, the bone graft material can fuse to the superior and inferior vertebral surfaces 22a and 22b of the intervertebral disc space 22. The at least one aperture 48 can extend through the upper and lower endplates 37 and 39. Thus, the at least one aperture 48 can be open to each of the first and second vertebral bodies 24 and 26. Further, the at least one aperture 48 can be open to the hollow interior. During operation, bone graft material can be packed inside the implant through one or both of the at least one side apertures 46 and the at least one vertical aperture 48. The bone graft material can fuse with the first and second vertebral bodies 24 and 26 through the upper and lower endplates 37 and 39.

In one example, the at least one aperture 48 that extends through the upper endplate 37 can be referred to as at least one upper bone graft aperture 48a. The at least one upper bone graft aperture 48a can include a plurality of upper bone graft apertures 48a. The upper bone graft apertures 48a can have different sizes as desired. For example, the upper bone graft aperture 48a can include at least one first upper bone graft aperture 50a and at least one second upper bone graft aperture 51a. The at least one first upper bone graft aperture 50a can be configured as a large aperture, and the at least one second upper bone graft aperture 51a can be configured as a small aperture. The at least one first upper bone graft aperture 50a defines a maximum first cross-sectional dimension along a plane that is defined by the longitudinal direction L and the lateral direction A. The at least one second upper bone graft aperture 51a define a second maximum cross-sectional dimension along the plane that is defined by the longitudinal direction L and the lateral direction A. The second cross-sectional dimension is smaller than the first cross-sectional dimension. The apertures 50a and 51a can be cylindrical, such that the cross-sectional dimensions of the apertures 50a and 51a can define diameters. It should be appreciated, however, that the apertures 50a and 51a can be sized and shaped as desired.

The at least one second upper bone graft aperture 51a can include a plurality of second upper bone graft apertures 51a that surround respective ones of the at least one first upper bone graft aperture 50a. The at least one first upper bone graft aperture 50a can include a plurality of first upper bone graft apertures 50a. The first upper bone graft apertures 50a can be at least partially aligned with each other along the longitudinal direction L. In one example, the respective geometric centers of the first upper bone graft apertures 50a can be aligned with each other along the longitudinal direction L. The first upper bone graft apertures 50a can also be equidistantly spaced from each other along the longitudinal direction L. Alternatively, the first upper bone graft apertures 50a can be spaced from each other at variable distances along the longitudinal direction L. Further, the large apertures 50 can be equidistantly spaced from the first and second side walls 34 and 36 with respect to the lateral direction A. While the implant 20 is illustrated as including three first upper bone graft apertures 50a, any number of first upper bone graft apertures 50a can be provided as desired. The first upper bone graft apertures 50a can all have the same maximum cross-sectional dimension or different maximum cross-sectional dimensions.

The second upper bone graft apertures 51a can be arranged about a perimeter of respective ones of the first upper bone graft apertures 50a. Thus, the first upper bone graft apertures 50a can be referred to as central upper bone graft apertures. The second upper bone graft apertures 51a can be referred to as peripheral upper bone graft apertures. The second upper bone graft apertures 51a can be arranged in several groups. The second upper bone graft apertures 51a of each group can surround the perimeter of a respective one of the first upper bone graft apertures 50a. For instance, a first group of second upper bone graft apertures 51a can be arranged about a first one of the first upper bone graft apertures 50a. The second upper bone graft apertures 51a of the first group can be equidistantly circumferentially spaced from each other. Further, the second upper bone graft apertures 51a of the first group can be spaced equidistantly from the first one of the first upper bone graft apertures 50a. Similarly, a second group of second upper bone graft apertures 51a can be arranged about a second one of the first upper bone graft apertures 50a. The second upper bone graft apertures 51a of the second group can be equidistantly circumferentially spaced from each other. Further, the second upper bone graft apertures 51a of the second group can be spaced equidistantly from the second one of the first upper bone graft apertures 50a. Similarly still, a third group of second upper bone graft apertures 51a can be arranged about a third one of the first upper bone graft apertures 50a. The second upper bone graft apertures 51a of the third group can be equidistantly circumferentially spaced from each other. Further, the second upper bone graft apertures 51a of the third group can be spaced equidistantly from the third one of the first upper bone graft apertures 50a. The second one of the first upper bone graft apertures 50a can be disposed between the first and third ones of the first upper bone graft apertures 50a along the longitudinal direction L It should be appreciated that one or more of the second upper bone graft apertures 51a can belong to more than one group. For instance, at least one of the second upper bone graft apertures 51a can belong to each of the first and second groups. In one example, first and second ones of the second upper bone graft apertures 51a can belong to each of the first and second groups. Further, at least one of the second upper bone graft apertures 51a can belong to the second and third groups. In one example, first and second ones of the second upper bone graft apertures 51a can belong to each of the second and third groups.

Similarly, the at least one aperture 48 that extends through the lower endplate 39 can be referred to as at least one lower bone graft aperture 48b. The at least one lower bone graft aperture 48b can include a plurality of lower bone graft apertures 48b. The lower bone graft apertures 48b can have different sizes as desired. For example, the lower bone graft aperture 48b can include at least one first lower bone graft aperture 50b and at least one second lower bone graft aperture 51b. The at least one first lower bone graft aperture 50b can be configured as a large aperture, and the at least one second lower bone graft aperture 51b can be configured as a small aperture. The at least one first lower bone graft aperture 50*b* defines a maximum first cross-sectional dimension along a plane that is defined by the longitudinal direction L and the lateral direction A. The at least one second lower bone graft aperture 51*b* define a second maximum cross-sectional dimension along the plane that is defined by the longitudinal direction L and the lateral direction A. The second cross-sectional dimension is smaller than the first cross-sectional dimension. The apertures 50*b* and 51*b* can be cylindrical, such that the cross-sectional dimensions of the apertures 50*b* and 51*b* can define diameters. It should be appreciated, however, that the apertures 50*b* and 51*b* can be sized and shaped as desired.

The at least one second lower bone graft aperture 51*b* can include a plurality of second lower bone graft apertures 51*b* that surround respective ones of the at least one first lower bone graft aperture 50*b*. The at least one first lower bone graft aperture 50*b* can include a plurality of first lower bone graft apertures 50*b*. The first lower bone graft apertures 50*b* can be at least partially aligned with each other along the longitudinal direction L. In one example, the respective geometric centers of the first lower bone graft apertures 50*b* can be aligned with each other along the longitudinal direction L. The first lower bone graft apertures 50*b* can also be equidistantly spaced from each other along the longitudinal direction L. Alternatively, the first lower bone graft apertures 50*b* can be spaced from each other at variable distances along the longitudinal direction L. Further, the large apertures 50 can be equidistantly spaced from the first and second side walls 34 and 36 with respect to the lateral direction A. While the implant 20 is illustrated as including three first lower bone graft apertures 50*b*, any number of first lower bone graft apertures 50*b* can be provided as desired. The first lower bone graft apertures 50*b* can all have the same maximum cross-sectional dimension or different maximum cross-sectional dimensions.

The second lower bone graft apertures 51*b* can be arranged about a perimeter of respective ones of the first lower bone graft apertures 50*b*. Thus, the first lower bone graft apertures 50*b* can be referred to as central lower bone graft apertures. The second lower bone graft apertures 51*b* can be referred to as peripheral lower bone graft apertures. Thus, the second lower bone graft apertures 51*b* can be arranged in several groups. The second lower bone graft apertures 51*b* of each group can surround the perimeter of a respective one of the first lower bone graft apertures 50*b*. For instance, a first group of second lower bone graft apertures 51*b* can be arranged about a first one of the first lower bone graft apertures 50*b*. The second lower bone graft apertures 51*b* of the first group can be equidistantly circumferentially spaced from each other. Further, the second lower bone graft apertures 51*b* of the first group can be spaced equidistantly from the first one of the first lower bone graft apertures 50*b*. Similarly, a second group of second lower bone graft apertures 51*b* can be arranged about a second one of the first lower bone graft apertures 50*b*. The second lower bone graft apertures 51*b* of the second group can be equidistantly circumferentially spaced from each other. Further, the second lower bone graft apertures 51*b* of the second group can be spaced equidistantly from the second one of the first lower bone graft apertures 50*b*. Similarly still, a third group of second lower bone graft apertures 51*b* can be arranged about a third one of the first lower bone graft apertures 50*b*. The second lower bone graft apertures 51*b* of the third group can be equidistantly circumferentially spaced from each other. Further, the second lower bone graft apertures 51*b* of the third group can be spaced equidistantly from the third one of the first lower bone graft apertures 50*b*. The second one of the first lower bone graft apertures 50*b* can be disposed between the first and third ones of the first lower bone graft apertures 50*b* along the longitudinal direction L.

It should be appreciated that one or more of the second lower bone graft apertures 51*b* can belong to more than one group. For instance, at least one of the second lower bone graft apertures 51*b* can belong to each of the first and second groups. In one example, first and second ones of the second lower bone graft apertures 51*b* can belong to each of the first and second groups. Further, at least one of the second lower bone graft apertures 51*b* can belong to the second and third groups. In one example, first and second ones of the second lower bone graft apertures 51*b* can belong to each of the second and third groups.

Each of the at least one upper bone graft aperture 48*a* can be aligned with a respective one of each the lower bone graft apertures 48*b* along the transverse direction T. Thus, the first and second upper bone graft apertures 50*a* and 51*a* can combine to define the same pattern as the pattern defined by the first and second lower bone graft apertures 50*b* and 51*b*. It should be appreciated, of course, that the first and second upper bone graft apertures 50*a* and 51*a* can combine to define any suitable first pattern as desired. Similarly, the first and second lower bone graft apertures 50*b* and 51*b* can define any suitable second pattern as desired that can be the same as the first pattern or different than the first pattern as desired. In one example, the bone graft apertures 48*a* and 48*b* can be arranged as in the intervertebral implant of the SynCage™ system.

With continuing reference to FIGS. 2-8, and as described above, the upper and lower endplates 37 and 39 can be made from Titanium or at least one Titanium alloy. The present disclosure recognizes that because Titanium is a harder material than PEEK, it is desirable for the upper outer surfaces 38 and the lower outer surface 40 to have a sufficient surface area to avoid subsidence of the intervertebral implant 20 when implanted in the intervertebral space.

The upper outer surface has an upper overall surface area in an outermost upper perimeter of the intervertebral implant. The outermost upper perimeter can be defined, in combination, by the leading end 30, the outer side surfaces of the first and second side walls 34 and 36, and the trailing end 32. The upper bone graft apertures 48*a*, including the first and second upper bone graft apertures 50*a* and 51*a*, combine to define an upper overall aperture area at the upper outer surface 38. The upper overall surface area and the upper overall aperture area combine to define an upper overall area. In one example, the upper overall aperture area can be between approximately 30% and 50% of the upper overall area. For instance, in one example, the upper overall aperture area can be approximately 40% of the upper overall area.

Similarly, the lower outer surface has a lower overall surface area in an outermost lower perimeter of the intervertebral implant 20. The outermost lower perimeter can be defined, in combination, by the leading end 30, the outer side surfaces of the first and second side walls 34 and 36, and the trailing end 32. The lower bone graft apertures 48*b*, including the first and second lower bone graft apertures 50*b* and 51*b*, combine to define an upper overall aperture area at the lower outer surface 40. The lower overall surface area and the lower overall aperture area combine to define a lower overall area. In one example, the lower overall aperture area can be between approximately 30% and 50% of the lower overall area. For instance, in one example, the lower overall aperture area can be approximately 40% of the lower overall area As illustrated in FIGS. 5-6, either or both of the upper outer surface 38 and the lower outer surface 40 can define a respective convexity. For instance, the upper outer surface 38 can define a convexity as it extends along one or both of the lateral direction A and the longitudinal direction L. Thus, the upper outer surface 38 can define a lateral convexity as it extends along the lateral direction A from one of the first and second side walls 34 and 36 to the other of the first and second side walls 34 and 36. For instance, the upper outer surface 38 can be curved from the first side wall 34 to the second side wall 36. The lateral convexity defined by the upper outer surface 38 can be disposed at the leading end 30, alternatively or additionally at the trailing end 32, and alternatively or additionally at a location between the leading end 30 to the trailing end 32. For instance, the convexity of the upper outer surface 38 can extend from the leading end 30 to the trailing end 32. Alternatively, the upper outer surface 38 can be substantially planar as it extends along the lateral direction from the first side wall 34 to the second side wall. Further, the upper outer surface 38 can define a longitudinal convexity as it extends along the longitudinal direction L from one of the leading end 30 and the trailing end 32 to the other of the leading end 30 and the trailing end 32. For instance, the upper outer surface 38 can be curved from the leading end 30 to the trailing end 32. Alternatively, the upper outer surface 38 can be substantially planar as it extends along the longitudinal direction L from the leading end 30 to the trailing end 32.

Similarly, the lower outer surface 40 can define a convexity as it extends along one or both of the lateral direction A and the longitudinal direction L. Thus, the lower outer surface 40 can define a lateral convexity as it extends along the lateral direction A from one of the first and second side walls 34 and 36 to the other of the first and second side walls 34 and 36. For instance, the lower outer surface 40 can be curved from the first side wall 34 to the second side wall 36. The lateral convexity defined by the lower outer surface 40 can be disposed at the leading end 30, alternatively or additionally at the trailing end 32, and alternatively or additionally at a location between the leading end 30 to the trailing end 32. For instance, the convexity of the lower outer surface 40 can extend from the leading end 30 to the trailing end 32. Alternatively, the lower outer surface 40 can be substantially planar as it extends along the lateral direction from the first side wall 34 to the second side wall. Further, the lower outer surface 40 can define a longitudinal convexity as it extends along the longitudinal direction L from one of the leading end 30 and the trailing end 32 to the other of the leading end 30 and the trailing end 32. For instance, the lower outer surface 40 can be curved from the leading end 30 to the trailing end 32. Alternatively, the lower outer surface 40 can be substantially planar as it extends along the longitudinal direction L from the leading end 30 to the trailing end 32.

Referring now to FIGS. 5-6, in one example the intervertebral implant 20 can define a lordotic profile. In particular, one or both of the upper and lower outer surfaces 38 and 40 can be sloped with respect to each other as they extend from the first side wall 34 to the second side wall 36. For instance, the first side wall 34 can be taller than the second side wall 36 along the transverse direction such that the implant 20. For instance, the first side wall 34 can have a first height along the transverse direction T that defines the height of the implant 20. The second side wall 36 can have a second height along the transverse direction T that is less than the first height. Because the second side wall 36 is disposed posterior of the first side wall 34 when the implant 20 is disposed in the intervertebral disc space 22, the second height can be referred to as a posterior height of the implant 20. It should be appreciated that the first and second heights can be configured such that the upper and lower outer surfaces 38 and 40 taper toward each other in a direction from the first side wall 34 to the second side wall 36. The tapered upper and lower outer surfaces 38 and 40 can define a lordotic profile that the implant 20 can impart onto the first and second vertebral bodies 24 and 26.

The lordotic profile can be configured as a lordotic angle defined by one or both of the first and second endplates 37 and 39, respectively. In this regard, it should be appreciated that the first side wall 34 can have a height greater than that of the posterior side 36 wall along the transverse direction T. Thus, the upper and lower endplates 37 and 39 define the lordotic angle with respect to each other as they extend along the lateral direction A. In particular, the lordotic profile can be at least partially defined the upper outer surface 38 that extends from the first side wall 34 to the second side wall 36. Further, the lordotic angle can be at least partially defined by the lower surface 40 that extends from the first side wall 34 to the second side wall 36. Thus, the lordotic profile can be configured as a lordotic angle defined by one or both of the upper and lower outer surfaces 38 and 40. The upper and lower outer surfaces 38 and 40 can define any suitable lorditic angle with respect to each other as desired as they extend in a direction from the first side wall 34 to the second side wall 36.

In one example, whether the upper and lower outer surfaces 38 and 40 are planar or non-planar, the angle can be defined by an upper straight line that extends from the uppermost end of the first side wall 34 to the uppermost end of the second side wall 36, and a lower straight line that extends from the lowermost end of the first side wall 34 to the lowermost end of the second side wall 36. Thus, the upper straight line can extend at least generally along the upper endplate 37. The lower straight line can extend at least generally along the lower endplate 39. The upper and lower straight lines can lie in a common plane that is defined by the transverse direction T and the lateral direction A. The uppermost ends of the first and second side walls 34 and 36 can define intersections with the upper endplate 37. The lowermost ends of the first and second side walls 34 and 36 can define intersections with the lower endplate 39. In one example, the lordotic angle can be approximately 8 degrees. It should be appreciated, of course, that the lordotic angle can be any suitable lordotic angle as desired. The term "approximate" or "substantial" as used herein with respect to measurements and directions recognizes that variations can be due, for instance, to manufacturing tolerances.

The intervertebral implant 20 can be configured to be attached to an insertion instrument that is configured to drive the implant 20 into the intervertebral space 22. For instance, the implant 20 can include an attachment hole 52 that is configured to receive an attachment rod of the insertion instrument. The attachment hole 52 can extend into the trailing end 32 in the insertion direction. Thus, the attachment hole 52 can extend into the trailing end 32 in a direction toward the leading end 30. The attachment hole 52 can be internally threaded so as to threadedly mate with a threaded attachment rod of the insertion instrument.

Alternatively or additionally, the implant 20 can include at least one attachment pocket 54 that is configured to receive a complementary attachment arm of an insertion instrument. In particular, the implant 20 can include first and second attachment pockets 54 that are spaced from each other along the lateral direction A. The first and second attachment pockets 54 can extend into the trailing end 32 in the insertion direction, and can also extend into the first and second side walls 34 and 36, respectively, along the lateral direction A. Thus, the first and second attachment pockets 54 can be open to both the trailing end 32 and to the first and second side walls 34 and 36, respectively. The first and second attachment pockets 54 can extend into the first and second side walls 34 and 36, respectively, to respective first and second inner surfaces 56 of the implant 20. The attachment hole 52 can be disposed between the first and second attachment pockets 54 with respect to the lateral direction A. Thus, the attachment hole 52 can be disposed between the first and second inner surfaces 56 that at least partially define the first and second pockets 54, respectively. The inner surfaces 56 can be scalloped or can define any suitable texture to assist in engagement with the respective attachment arms of the insertion instrument.

In one example, the implant 20 can engage the insertion instrument as in the Oracle® Cage system. In another example, the implant 20 can engage the insertion instrument as in the Cougar® LS implant system from DePuy Synthes, Inc, a company of Johnson and Johnson having a place of business in New Brunswick, N.J. It should further be appreciated that the implant 20 can attach to an insertion instrument that does not attach to the implant 20 in the attachment hole 52. Such instruments are described in U.S. Pat. No. 8,308,734. For instance, the insertion instrument can include a pusher member that abuts the trailing end of the implant 20, and further includes first and second arms that extend into the first and second attachment pockets 54. The pusher member can apply a force that urges the implant 20 to translate between upper and lower arms of the insertion instrument and into the intervertebral space 22. As is the case with the insertion instruments discloser herein, once the implant 20 is disposed in the intervertebral space 22 at the desired position in the desired location, the insertion instrument can be detached from the implant 20.

In this regard, an implant kit can include the implant 20 and the insertion instrument. Method steps for inserting the intervertebral implant 20 into the intervertebral space 22 in the manner described above are also contemplated by the present disclosure.

Figure 12:
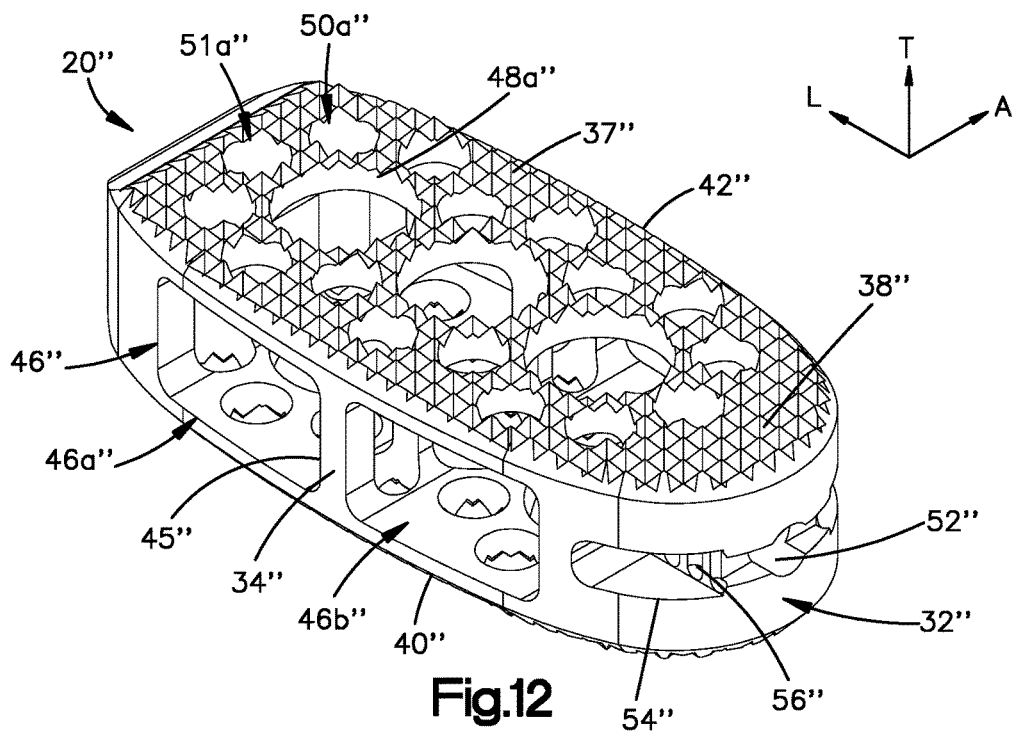
FIG. 12 is a perspective view of an intervertebral implant similar to the intervertebral implant illustrated in FIG. 1, but having parallel upper and lower endplate surfaces in accordance with another alternative embodiment.
Figure 13:
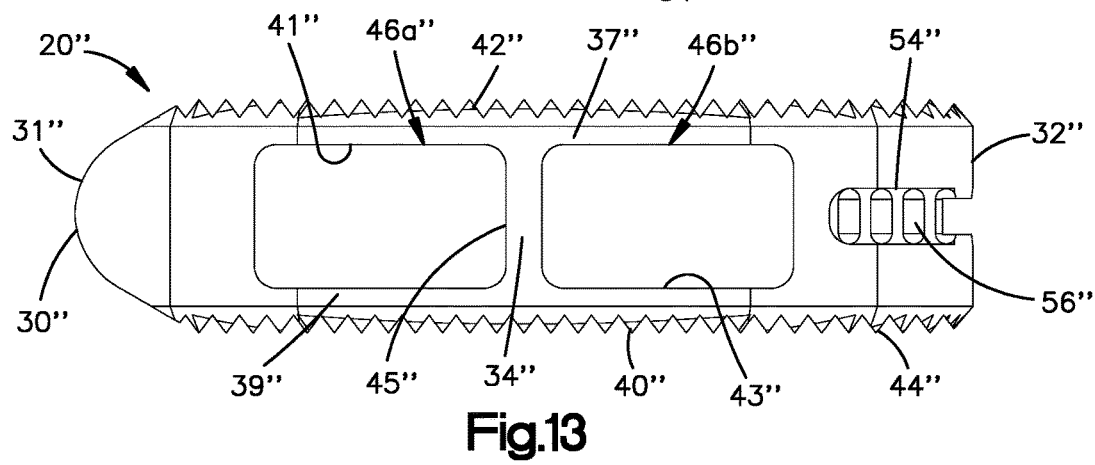
FIG. 13 is a side elevation view of the intervertebral implant illustrated in FIG. 12.
Figure 14:
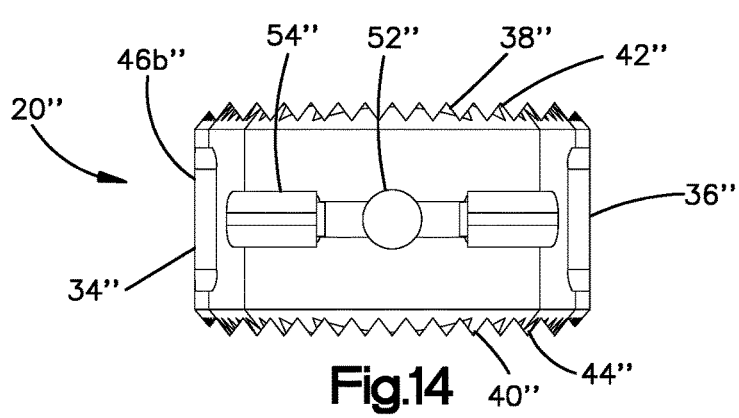
FIG. 14 is a rear end elevation view of the intervertebral implant illustrated in FIG. 12.

Referring now also to FIGS. 2-14 generally, it is recognized that a kit of intervertebral implants 20 can be provided. The intervertebral implant 20 described above with respect to FIGS. 2-8 can be provided as a first intervertebral implant of the kit. FIGS. 9-11 illustrate a second intervertebral implant 20' of the kit. FIGS. 12-14 illustrate a third intervertebral implant 20" of the kit. It should be appreciated that the kit can include any number of intervertebral implants as desired, and that the intervertebral implants 20, 20', and 20" are merely representative of intervertebral implants that can be included in the kit. The second and third intervertebral implants 20' and 20" can be constructed as described above with respect to FIGS. 2-8 unless otherwise indicated. Accordingly, the second intervertebral implant 20' as illustrated in FIGS. 9-11 include second components identified with reference numbers in common with like components of the first intervertebral implant 20 illustrated in FIGS. 2-8 which can be designated as first components, but bearing an apostrophe. Similarly, the third intervertebral implant 20" as illustrated in FIGS. 12-14 include third components identified with reference numbers in common with like first components of the first intervertebral implant 20 illustrated in FIGS. 2-8, but bearing a double apostrophe.

One or more of the intervertebral implants of the kit can define a lordotic angle that is greater than one or more others of the intervertebral implants of the kit. For instance, referring now to FIGS. 9-11, the second intervertebral implant 20' can have a second lordotic profile that is different than the lordotic profile of the first intervertebral implant 20. In this regard, the lordotic profile of the first intervertebral implant 20 can be referred to as a first lordotic profile. Similarly, the lordotic angle defined by the upper and lower outer surfaces 38 and 40 of the first intervertebral implant 20 can be referred to as a first lordotic angle.

In one example, the second lordotic profile can be configured as a second lordotic angle defined by one or both of the first and second endplates 37' and 39' as described above with respect to the first intervertebral implant 20. Thus, the second lordotic profile can be configured as a second lordotic angle defined by one or both of the upper and lower outer surfaces 38' and 40'. In particular, the upper and lower outer surfaces 38' and 40' can define any suitable angle with respect to each other as desired as they extend in a direction from the respective first side wall 34' to the respective second side wall 36'. As described above with respect to the first intervertebral implant 20, whether the upper and lower outer surfaces 38' and 40' are planar or non-planar, the lordotic angle can be defined by an upper straight line that extends from the uppermost end of the first side wall 34' to the uppermost end of the second side wall 36', and a lower straight line that extends from the lowermost end of the first side wall 34' to the lowermost end of the second side wall 36'. In one example, the second lordotic angle can be approximately 14 degrees. It should be appreciated, of course, that the second lordotic angle can be any suitable lordotic angle as desired. In one example, the second lordotic angle can be greater than the first lordotic angle. Further, a plurality of the intervertebral implants of the kit can define lordotic angles greater than the first lordotic angle. Alternatively, the second lordotic angle can be less than the first lordotic angle. Further, a plurality of the intervertebral implants of the kit can define lordotic angles greater than the first lordotic angle.

Referring now to FIGS. 12-14, the third intervertebral implant 20" of the kit can be devoid of a lordotic profile. In particular, the first and second endplates 37" and 39" of the third intervertebral implant 20" can be configured so as to not define a lordotic angle. Thus, the upper and lower outer surfaces 38' and 40' can be oriented substantially parallel to each other as they extend along the lateral direction A. Thus, the first and second side walls 34 and 36 can define the same height along the transverse direction T. As a result, the uppermost ends of the first and second side walls 34 and 36 can be aligned with each other along the lateral direction A. Similarly, the lowermost ends of the first and second side walls 34 and 36 can be aligned with each other along the lateral direction. Accordingly, an upper straight line that extends from the uppermost end of the first side wall 34 to the uppermost end of the second side wall 36 can be oriented parallel with a lower straight line that extends from the lowermost end of the first side wall 34 to the lowermost end of the second side wall 36 Further, it should be appreciated that a plurality of the intervertebral implants of the kit can be devoid of a lordotic angle.

It is recognized that the endplates made of Titanium have a hardness that is greater than the hardness of endplates made of PEEK. Accordingly, it can desirable to avoid increasing the thickness of the endplates 37 and 39 to a degree such that the endplates 37 and 39 become too stiff. Accordingly, at least respective portions of the first endplates 37 and 39 of the first intervertebral implant 20, the second endplates 37' and 39' of the second intervertebral implant 20', and the third endplates 37" and 39" of the third intervertebral implant 20" can have the same thickness. The respective thicknesses of the endplates 37 and 39 can be measured along the transverse direction T. In one example, the respective upper thicknesses of the first upper endplate 37, the second upper endplate 37', and the third upper endplate 37" can be substantially equal to each other, regardless of the lordotic profile or lack thereof of the respective intervertebral implant. Similarly, the respective lower thicknesses of the first lower endplate 39, the second lower endplate 39', and the third lower endplate 39" can be substantially equal to each other, regardless of the lordotic profile or lack thereof of the respective intervertebral implant. Further, the respective upper and lower thicknesses can be constant along a substantial entirety of the respective endplates. Further still, the upper thickness can be substantially equal to the lower thickness.

The upper and lower thicknesses can be measured at an intersection with the respective upper and lower endplates and the respective anterior side walls. As described above, the implants can include side apertures 46, 46', and 46", respectively, that extend through the respective first side walls 34, 34', and 34". The thickness of the upper and lower endplates can be measured at a location that is aligned with the respective side aperture that extends through the respective first side wall (also referred to as an anterior side aperture). The thicknesses can be measured from the outer surface of the respective endplate to the inner surface of the respective endplate along the transverse direction T.

The height of the first side wall 34' of the second intervertebral implant 20' can be greater than the height of the first side wall 34 of the first intervertebral implant 20. However, because the upper endplates 37 and 37' have the same thickness, and the lower endplates 39 and 39' have the same thickness, the first and second side apertures 46 and 46' can have different heights. In particular, the side aperture 46' of the second intervertebral implant 20' that extends through the anterior side wall 34' can have a second height along the transverse direction T that is greater than a first height of the side aperture 46 of the first intervertebral implant that extends through the anterior side wall 34. Thus, the anterior side aperture of the first intervertebral implant 20 can define a first area along the respective first side wall 34, and the anterior side aperture of the second intervertebral implant 20' can define a second area along the respective side wall 34' that is greater than the first area. Similarly, the third side aperture 46" of the third intervertebral implant 20" that extends through the anterior side wall 34" can have a third height along the transverse direction T that is less than the first height of the side aperture 46 of the first intervertebral implant 20. Thus, the anterior side aperture of the third intervertebral implant 20" can define a third area along the respective side wall 34" that is less than the first area along of the first intervertebral implant 20.

As described above, the lordotic profile of each of the implants of the kit can be the same or different than one or more other intervertebral implants of the kit. Alternatively or additionally, one or more the intervertebral implants 20 of the kit can be sized differently than each other. For instance, one or more of the intervertebral implants 20 of the kit have a length along the longitudinal direction L that is than one or more others of the intervertebral implants 20 of the kit. The length can be measured from the respective leading end to the respective trailing end along the longitudinal direction. By way of example, the lengths of the intervertebral implants of the kit can be in the range between and including approximately 40 mm and approximately 60 mm, including approximately 40 mm, approximately 45 mm, approximately 50 mm, approximately 55 mm, and approximately 60 mm. It should be appreciated, of course, that the intervertebral implants of the kit can have any suitable length as desired. Alternatively or additionally, one or more of the intervertebral implants 20 of the kit can have a width along the lateral direction A that is greater than the others of the intervertebral implants 20 of the kit. The width can be measured from the respective first side wall to the respective second side wall along the lateral direction A. By way of example, the widths of the intervertebral implants of the kit can be in the range between and including approximately 20 mm and approximately 30 mm, including approximately 22 mm and approximately 26 mm. It should be appreciated, of course, that the intervertebral implants of the kit can have any suitable width as desired.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. It is understood, therefore, that this invention is not limited to the particular embodiments disclosed, but it is intended to cover modifications within the spirit and scope of the present disclosure. Further, it should be appreciated, that the term substantially indicates that certain directional components are not absolutely perpendicular to each other and that substantially perpendicular means that the direction has a primary directional component that is perpendicular to another direction.

What is claimed:

1. A kit of intervertebral implants each configured to be inserted into an intervertebral space, each intervertebral implant of the kit comprising:
   a leading end and a trailing end, arranged such that the leading end is spaced from the trailing end in an insertion direction into the intervertebral space;
   an anterior side wall and a posterior side wall each extending between the leading end and the trailing end, wherein the anterior and posterior side walls are opposite each other along a lateral direction that is perpendicular to the insertion direction; and
   upper and lower endplates each made of Titanium or an alloy thereof and spaced from each other along a transverse direction that is perpendicular to each of the insertion direction and the lateral direction, the endplates defining respective outer surfaces that are configured to abut respective superior and inferior vertebral bodies when the implant is disposed in the intervertebral space,
   wherein the anterior side wall of a first intervertebral implant of the kit has a height greater than that of the posterior side wall along the transverse direction, such that the upper and lower endplates of the first intervertebral implant define a first angle with respect to each other as they extend along the lateral direction, and each of the upper and lower endplates of the first intervertebral implant define respective thicknesses at the anterior side wall,
   wherein the anterior side wall of a second intervertebral implant of the kit has a height greater than that of the posterior side wall along the transverse direction, such that the upper and lower endplates of the second intervertebral implant define a second angle with respect to each other as they extend along the lateral direction that is greater than the first angle, and wherein 1) the upper and lower endplates of the first intervertebral implant define respective inner surfaces that face each other, 2) the upper and lower endplates of the first intervertebral implant define respective thicknesses from the respective inner surfaces to the respective outer surfaces, 3) the upper and lower endplates of the second intervertebral implant define respective inner surfaces that face each other, 4) the upper and lower endplates of the second intervertebral implant define respective thicknesses from the respective inner surfaces to the respective outer surfaces, and 5) the respective thicknesses of the upper and lower endplates of the second intervertebral implant at the anterior side wall are equal to the respective thicknesses of the upper and lower endplates of the first intervertebral implant at the anterior side wall.

2. The kit as recited in claim 1, wherein each of the intervertebral implants defines an anterior side aperture that extends through the anterior side wall along the lateral direction, and the respective thicknesses of the upper and lower endplates of the first and second intervertebral implants are measured at a location aligned with the anterior side aperture.

3. The kit as recited in claim 2, wherein the anterior side aperture of the first intervertebral implant defines a first area along the respective anterior side wall, and the anterior side aperture of the second intervertebral implant defines a second area along the respective anterior side wall that is greater than the first area.

4. The kit as recited in claim 2, wherein the anterior side aperture of the first intervertebral implant defines a first height along the transverse direction, and the anterior side aperture of the second intervertebral implant defines a second height along the transverse direction that is greater than the first height.

5. The kit as recited in claim 2, wherein each of the intervertebral implants defines first and second anterior side apertures that extend through the anterior side wall along the lateral direction, the first and second side apertures separated from each other by a transverse rib that extends from the superior endplate to the inferior endplate, and the transverse rib of the second implant has a thickness along the insertion direction that is greater than that of the first implant.

6. The kit as recited in claim 1, wherein the first angle is approximately 8 degrees.

7. The kit as recited in claim 6, wherein the second angle is approximately 14 degrees.

8. The kit as recited in claim 1, wherein the upper and lower endplates define respective inner surfaces opposite the respective outer surfaces, and the thicknesses are measured from the respective outer surfaces to the respective inner surfaces.

9. The kit as recited in claim 1, wherein the anterior side wall of a third intervertebral implant of the kit has a height substantially equal to that of the posterior side wall, such that the upper and lower endplates of the third intervertebral implant are oriented substantially parallel to each other, and each of the upper and lower endplates of the third intervertebral implant define respective thicknesses at the anterior side wall that is equal to the respective thicknesses of the upper and lower endplates of each of the first and second intervertebral implants at the anterior side wall.

10. The kit as recited in claim 1, wherein each of the upper and lower endplates of the intervertebral implants defines respective bone graft apertures extending therethrough along the transverse direction, wherein the bone graft apertures include a plurality of central bone graft apertures, and a plurality of peripheral bone graft apertures that surround the central bone graft apertures.

11. The kit as recited in claim 10, wherein the peripheral bone graft apertures are spaced at equal distances from at least one of the central bone graft apertures.

12. The kit as recited in claim 11, wherein respective centers of the central bone graft apertures are aligned with each other along the longitudinal direction.

13. The kit as recited in claim 12, wherein the central bone graft apertures are larger than the peripheral bone graft apertures.

14. The kit as recited in claim 1, wherein the leading end defines a nose that is tapered with respect to both the lateral direction and the transverse direction.

15. A kit of intervertebral implants each configured to be inserted into an intervertebral space, each intervertebral implant of the kit comprising:
    a leading end and a trailing end, arranged such that the leading end is spaced from the trailing end in an insertion direction into the intervertebral space;
    an anterior side wall and a posterior side wall each extending between the leading end and the trailing end, wherein the anterior and posterior side walls are opposite each other along a lateral direction that is perpendicular to the insertion direction, wherein each of the intervertebral implants defines an anterior side aperture that extends through the anterior side wall; and
    upper and lower endplates each made of Titanium or an alloy thereof and spaced from each other along a transverse direction that is perpendicular to each of the insertion direction and the lateral direction, each of the endplates defining a respective outer surface that is configured to abut respective superior and inferior vertebral bodies when the implant is disposed in the intervertebral space,
    wherein the upper and lower endplates of a first intervertebral implant of the kit converge toward each other at a first angle as they extend along the lateral direction from the anterior side wall toward the posterior side wall,
    wherein the upper and lower endplates of a second intervertebral implant of the kit converge toward each other at a second angle as they extend along the lateral direction from the anterior side wall toward the posterior side wall, and
    wherein the second angle is greater than the first angle, and the anterior side aperture of the second intervertebral implant has a height along the transverse direction that is greater than that of the anterior side aperture of the first intervertebral implant.

16. A kit of intervertebral implants each configured to be inserted into an intervertebral space, each intervertebral implant of the kit comprising:
    a leading end and a trailing end, arranged such that the leading end is spaced from the trailing end in an insertion direction into the intervertebral space;
    an anterior side wall and a posterior side wall each extending between the leading end and the trailing end, wherein the anterior and posterior side walls are opposite each other along a lateral direction that is perpendicular to the insertion direction, wherein each of the intervertebral implants defines first and second anterior side apertures that extend through the anterior side wall; and upper and lower endplates each made of Titanium or an alloy thereof and spaced from each other along a transverse direction that is perpendicular to each of the insertion direction and the lateral direction, each of the endplates defining a respective outer surface that is configured to abut respective superior and inferior vertebral bodies when the implant is disposed in the intervertebral space, a rib that extends from the upper endplate to the lower endplate between the first and second anterior side apertures so as to separate the first and second anterior side apertures from each other, wherein the upper and lower endplates of a first intervertebral implant of the kit converge toward each other at a first angle as they extend along the lateral direction from the anterior side wall toward the posterior side wall, wherein the upper and lower endplates of a second intervertebral implant of the kit converge toward each other at a second angle as they extend along the lateral direction from the anterior side wall toward the posterior side wall, and wherein the second angle is greater than the first angle, and the rib of the second intervertebral implant has a thickness along a direction perpendicular to the transverse direction that is greater than that of the rib of the first intervertebral implant.

17. The kit as recited in claim 16, wherein the first and second angles are in a range from approximately zero degrees to approximately 14 degrees.

18. The kit as recited in claim 16, wherein the thickness is measured along the insertion direction.

19. The kit as recited in claim 16, wherein the first intervertebral implant of the kit has a first length along the longitudinal direction from the leading end to the trailing end, and the second intervertebral implant of the kit has a second length along the longitudinal direction from the leading end to the trailing end that is greater than the first length.

20. The kit as recited in claim 19, wherein the first and second lengths are in a range from approximately 40 mm to approximately 60 mm.

\* \* \* \* \*